US00PP32378P2

(12) United States Plant Patent
Brown

(10) Patent No.: US PP32,378 P2
(45) Date of Patent: Oct. 20, 2020

(54) ***DELOSPERMA* PLANT NAMED 'DDDYE04-0'**

(50) Latin Name: *Delosperma cooperi*
Varietal Denomination: DDDYE04-0

(71) Applicant: NuFlora International Pty. Ltd., Macquarie Fields (AU)

(72) Inventor: Graham Brown, Pennant Hills (AU)

(73) Assignee: NuFlora International Pty Ltd (AU)

( * ) Notice: Subject to any disclaimer, the term of this patent is extended or adjusted under 35 U.S.C. 154(b) by 0 days.

(21) Appl. No.: 16/602,866

(22) Filed: Dec. 12, 2019

(51) Int. Cl.
*A01H 5/02* (2018.01)
*A01H 6/00* (2018.01)

(52) U.S. Cl.
USPC ..... Plt./422

(58) Field of Classification Search
USPC ..... Plt./263.1, 422
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Delosperma* plant named 'DDDYE04-0' is disclosed, characterized by abundant large, yellow flowers occurring throughout the plant. Plants have a low, mounding habit, and are tolerant to cold. The new variety is a *Delosperma*, normally produced as an outdoor garden or container plant.

2 Drawing Sheets

Latin name of the genus and species: *Delosperma cooperi.*

Variety denomination: 'DDDYE04-0'.

BACKGROUND OF THE INVENTION

The new *Delosperma* cultivar is a product of open pollination by the inventor at a commercial nursery in NSW, Australia. The open pollination was made in October 2016.

Various unnamed, unpatented proprietary *Delosperma* varieties were planted in open-pollination crossing blocks and the resulting seed bulk collected. Parent varieties are unidentified. The new variety was selected in October 2017 by the inventor in a group of seedlings at the same nursey in Cobbitty, NSW, Australia.

Asexual reproduction of the new cultivar 'DDDYE04-0' by terminal vegetative cuttings was first performed at a greenhouse in Cobbitty, NSW, Australia in October 2017, and has shown that the unique features of this cultivar are stable and reproduced true to type in 6 successive generations.

SUMMARY OF THE INVENTION

The cultivar 'DDDYE04-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DDDYE04-0' These characteristics in combination distinguish 'DDDYE04-0' as a new and distinct *Delosperma* cultivar:

1. Bright yellow flowers.
2. Low, mounded habit.

3. Cold tolerance to USDA Zone 5.
4. Large flowers.
5. Flowering throughout plant, not just on tips.
6. Drought tolerance.

PARENT COMPARISON

The seed parents are not identifiable.

COMMERCIAL COMPARISON

Plants of the new cultivar 'DDDYE04-0' are comparable to the variety *Delosperma* 'WOWD2011-1', U.S. Plant Pat. No. 25,684. The two *Delosperma* varieties are similar in most horticultural characteristics, however, the new variety 'DDDYE04-0' differs in the following:

1. The new variety has better cold tolerance than this comparator.
2. The new variety flowers more in Summer than this comparator.

BRIEF DESCRIPTION OF THE PHOTOGRAPHS

Figure 1:
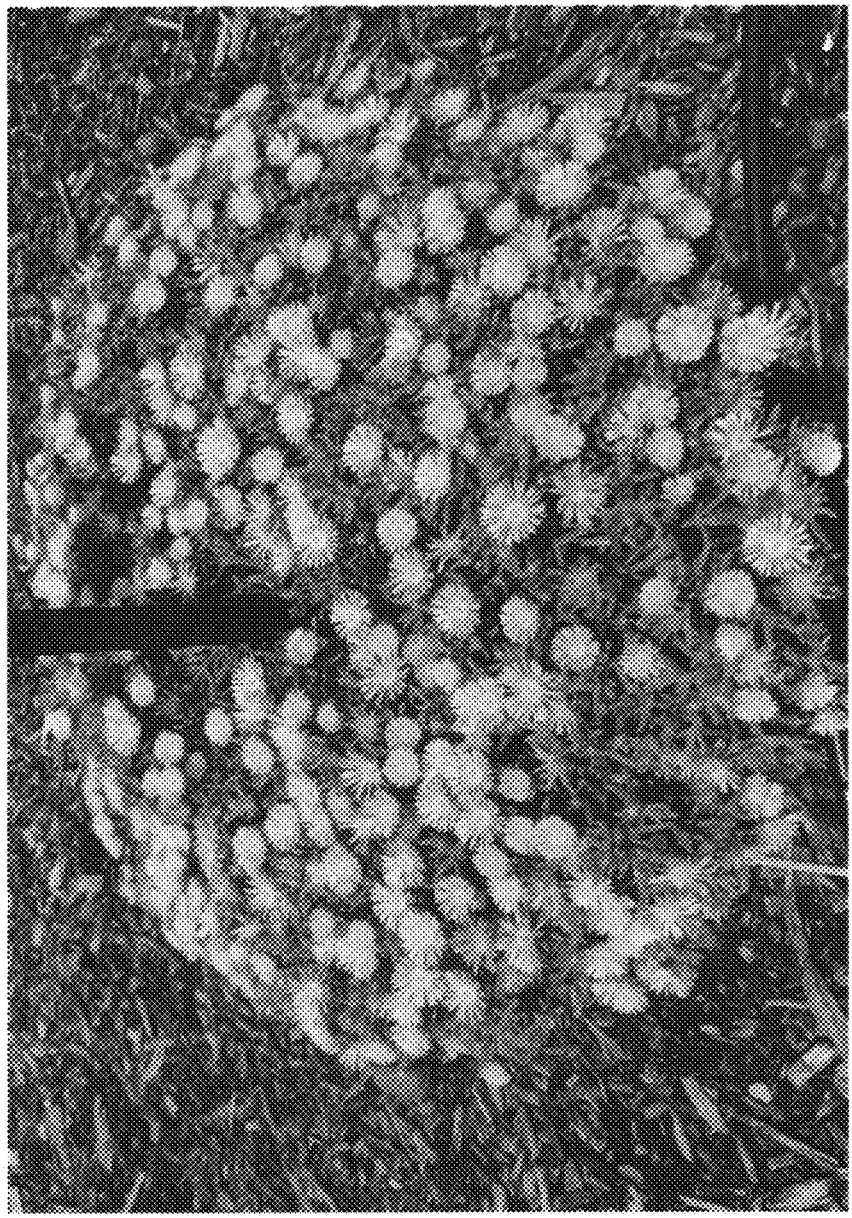

The accompanying photograph in FIG. 1 illustrates in full color a typical plant of 'DDDYE04-0' grown in a nursery in the ground. Age of the plant photographed is approximately 8 months from a rooted cutting.

Figure 2:
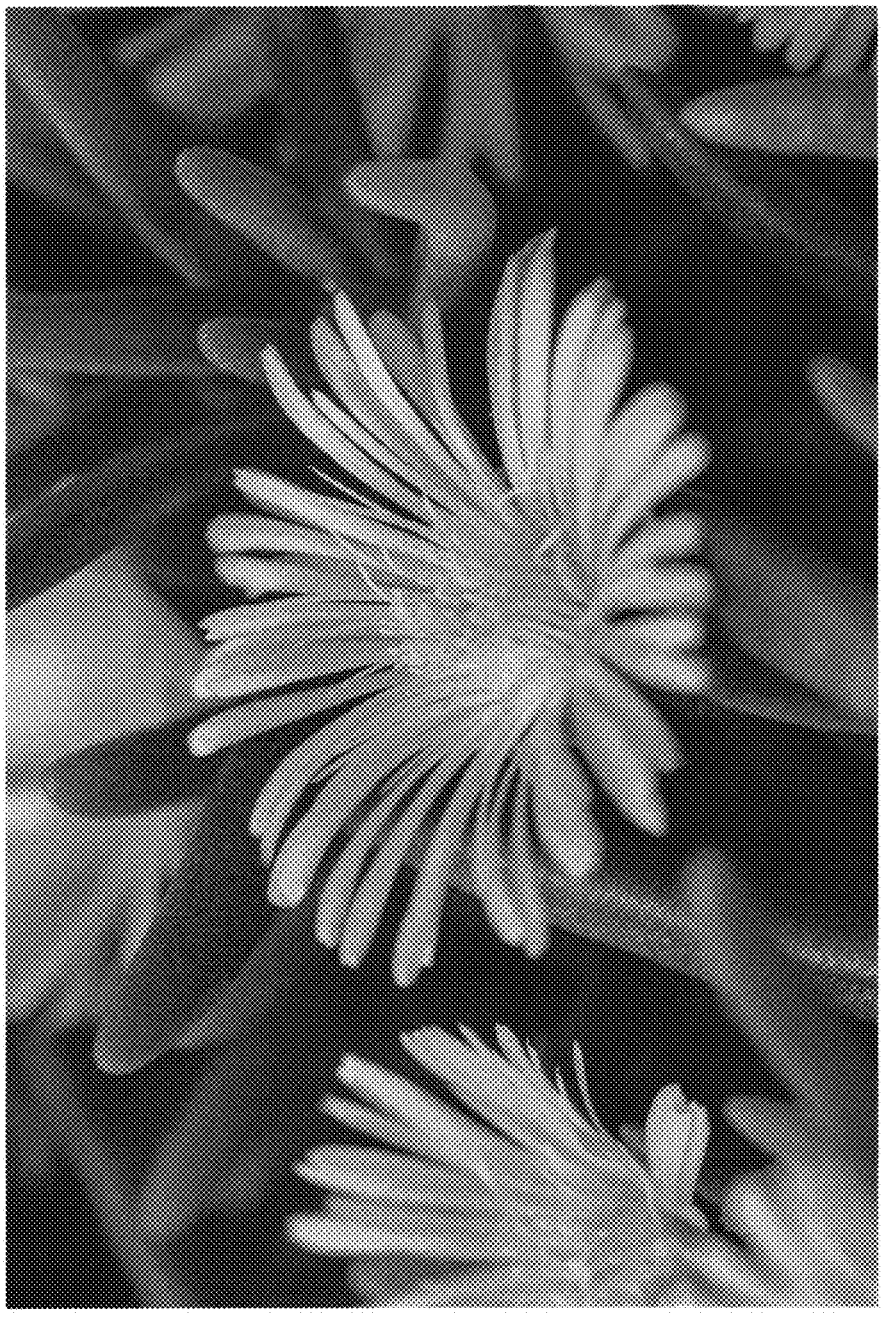

FIG. 2 illustrates in full color a close up of typical blooms of 'DDDYE04-0'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'DDDYE04-0' plants grown from Winter to Spring in moderate climate in a greenhouse, in Santa Paula, Calif. The growing temperature ranged from approximately 16° C. to 30° C. during the day and from 9° C. to 16° C. during the night. General light conditions are high light levels 60,000 to 90,000 Lux Measurements and numerical values represent averages of typical plant types.

Botanical classification: *Delosperma cooperi* 'DDDYE04-0'.

PROPAGATION

Type of propagation typically used: Terminal vegetative cuttings.

Root description: Thin, fibrous, freely branching. Near RHS Greyed-Yellow 161D in color.

PLANT

Age of plant described: Approximately 10 weeks.

Container size of the plant described: 5 inch.

Growth habit: Trailing plant with a mounded center. Tender annual.

Height: Approximately 10 cm.

Plant spread: Approximately 32 cm.

Growth rate: Moderate.

Branching characteristics: Very freely branching.

Approximate quantity of lateral branches: Approximately 14 to 22 primary lateral branches, subsequently dividing into numerous secondary and tertiary lateral branches.

Length of lateral branches: Approximately 7 to 116 cm.

Diameter of lateral branches: Approximately 3 mm.

Shape of lateral branches: Round.

Substance of lateral branches: Succulent.

Texture of lateral branches: Moderately glossy, moderately dense coverage of short glandular hairs. Density increases towards terminal end. Hairs about 1 mm in diameter and height. Colored near RHS White 155A.

Lateral branch strength: Somewhat weak and moderately flexible.

Lateral branch color: Lower surfaces colored near RHS Greyed-Orange 174C. Upper surfaces near Greyed-Orange 174A.

Internode length: Average range 2.5 to 3.5 cm.

FOLIAGE

Leaf:

- *Arrangement*.—Opposite.
- *Quantity*.—4 to 10 pairs, depending upon length of branch.
- *Shape of blade*.—Ligulate, triangular in cross-section.
- *Aspect*.—Reflexed downward, single center wedged indentation along length of approximately 80% of blade.
- *Average length*.—Average range 3.0 to 3.5 cm.
- *Average width*.—Approximately 4 to 5 mm.
- *Average depth*.—3 to 4 mm.
- *Apex*.—Acute.
- *Base*.—Cuneate.
- *Attachment*.—Sessile.
- *Margin*.—Entire.
- *Texture of top surface*.—Glabrous, to very slightly rough with reduced glandular structures.
- *Texture of bottom surface*.—Glabrous to very slightly rough with reduced glandular structures.
- *Color*.—Young foliage upper side: Near RHS Green 137B. Young foliage under side: Near RHS Green 137C. Mature foliage upper side: Near RHS Green 137B. Mature foliage under side: Near RHS Green 138A.
- *Venation*.—Indistinguishable from foliage blade.
- *Petiole*.—Not present.

FLOWER

Bloom period:

- *Natural season*.—Long lasting flowering period. From March through December in Santa Paula, Calif.
- *In commercial production, flowering begins from a rooted cutting*.—Approximately 6 to 8 weeks.

Inflorescence:

- *Type*.—Single rotate terminally occurring flowers. Usually 2 single flowers per node.

Bud:

- *Bud shape*.—Ovate.
- *Bud length*.—Approximately 10 mm.
- *Bud diameter*.—Approximately 6 mm.
- *Bud color*.—Near RHS Yellow 12B flushed Orange-Red 34B.
- *Rate of opening*.—Individual flowers: Fully open approximately 2 days from the bud showing color stage.

Individual flower:

- *Type of individual flowers*.—Simple, rotate.
- *Shape*.—Radial.
- *Quantity of flowers and buds per plant*.—2 per node 4 to 16 flowers and buds per lateral branch on a plant of this age in a 5 inch pot.
- *Diameter of entire flower*.—Average range 2.85 to 3.0 cm.
- *Depth of flower*.—Approximately 1.2 cm.
- *Flower longevity on plant*.—Approximately 8 to 10 days.
- *Persistent or self-cleaning*.—Persistent.
- *Fragrance*.—Moderate, musty scent.

Petals:

- *Quantity*.—Average range 35 to 45.
- *Length of petal*.—Average range 1.2 to 1.5 cm.
- *Width of petal*.—Approximately 2 mm.
- *Apex*.—Rounded.
- *Base*.—Tapered.
- *Shape of petal*.—Strap-like.
- *Petal margin*.—Entire.
- *Petal arrangement*.—Radial, forming 2 whorls around stamens and petaloids.
- *Petal appearance*.—Very shiny, iridescent upper surface. Lower surface very shiny.
- *Petal texture*.—Smooth, glabrous upper and lower surfaces.

Color:

- *Upper surface at first opening*.—Near RHS Yellow 13A, base near Yellow 11D.
- *Upper surface at maturity*.—Near RHS Yellow-Orange 15A, midsection near Yellow-Orange 14B, base near Yellow 13D.
- *Upper surface at fading*.—Near RHS Yellow-Orange 15C, apex flushed Yellow-Orange 24B, base near Yellow 11D.

*Under surface at first opening*.—Apex near RHS Yellow 13A, fading to 12B, then 12A, base near Yellow 11D.

*Under surface at maturity*.—Near RHS Yellow 13B, apex near Yellow-Orange 17A, base near Yellow 13D.

*Under surface at fading*.—Near RHS Yellow-Orange 14A apex flushed Yellow-Orange 24B, base near Yellow 11D.

Petaloids:

*Quantity*.—Average range 15 to 25.

*Length*.—Approximately 3 to 5 mm.

*Width*.—Approximately 1.0 mm.

*Apex*.—Acute.

*Base*.—Tapered.

*Shape*.—Linear.

*Margin*.—Entire.

*Arrangement*.—Radially around stamens.

*Petal appearance*.—Shiny, iridescent all surfaces.

*Petal texture*.—Smooth, glabrous upper and lower surfaces.

Color:

*Upper surface at first opening*.—Near RHS Yellow 10A.

*Upper surface at maturity*.—Near RHS Yellow 12A.

*Upper surface at fading*.—Near RHS Yellow 12C.

*Under surface at first opening*.—Near RHS Yellow 10A.

*Under surface at maturity*.—Near RHS Yellow 12A.

*Under surface at fading*.—Near RHS Yellow 12C.

Calyx: Rotate, 10 mm in depth, 1.7 in diameter(with sepals fully expanded).

Sepal:

*Number*.—5.

*Sepal arrangement*.—5 sepals in a single whorl.

*Sepal length*.—Average range 5 to 7 mm.

*Sepal width*.—Average range 2 to 3 mm.

*Sepal shape*.—Narrow deltate.

*Base*.—Fused.

*Apex shape*.—Acute.

*Margin*.—Entire.

*Sepal appearance*.—Matte, upper and lower surfaces.

*Texture*.—Glabrous, upper and lower surfaces.

*Color*.—Upper: Near RHS Green 137A. Lower: Near RHS Green 137A.

Peduncle:

*Length*.—Average range 10 to 15 mm.

*Diameter*.—Approximately 3 mm.

*Aspect*.—Slightly curved and undulating.

*Strength*.—Weak and flexible.

*Texture*.—Covered in very short glandular hairs.

*Color*.—Near RHS Yellow-Green 144C, flushed Greyed-Red 179B.

REPRODUCTIVE ORGANS

Number of pistils per flower: 5.

*Pistil length*.—Approximately 2 mm. Highly reduced, style and stigma indistinguishable. All structures colored near RHS Green-Yellow 1C.

*Stamens quantity*.—Average 40.

*Stamen length*.—3 to 4 mm.

*Anther shape*.—Elliptic.

*Anther size*.—0.5 mm.

*Anther color*.—Near RHS Yellow 7C.

*Pollen color*.—Near RHS Yellow 7B.

*Pollen quantity*.—Moderate.

OTHER CHARACTERISTICS

Disease resistance: *Delosperma cooperi* is recognized to be generally not susceptible to diseases and pests. The new cultivar shows neither resistance nor susceptibility to diseases and pests which might be found on *Delosperma*. Especially in conditions of too much soil moisture, crown rot might occur, most likely caused by *Phytophthora*. Potential pests include the *Aphis* genus and the family *Pseudococcidae* (mealybug).

Environmental tolerance: Typically USDA Zones 3 through 9. Plants are also tolerant to drought.

Fruits and seeds: Not observed to date.

What is claimed is:

1. A new and distinct cultivar of *Delosperma* plant named 'DDDYE04-0' as herein illustrated and described.

* * * * *